United States Patent
Takemoto

(12) 
(10) Patent No.: US 6,316,657 B1
(45) Date of Patent: Nov. 13, 2001

(54) PROCESS FOR PURIFICATION OR RECOVERY OF SWEETENER

(75) Inventor: Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/525,319

(22) Filed: Mar. 13, 2000

(30) Foreign Application Priority Data

Sep. 12, 1997 (JP) .................................................... 9-247941
Aug. 19, 1998 (WO) ..................................... PCT/JP98/03682

(51) Int. Cl.$^7$ ................................................. C07C 229/00
(52) U.S. Cl. ............................................. 560/41; 560/40
(58) Field of Search ......................................... 560/40, 41

(56) References Cited

U.S. PATENT DOCUMENTS

| | | |
|---|---|---|
| 5,480,668 | 1/1996 | Nofre et al. . |
| 5,510,508 * | 4/1996 | Claude et al. . |
| 5,728,862 | 3/1998 | Praskash . |

FOREIGN PATENT DOCUMENTS

A-8-503206   4/1996   (JP) .

OTHER PUBLICATIONS

Ault, Addison. Techniques and Experiments for Organic Chemistry, Fifth Edition. Waveland Press Inc., pp 110–111, 1994.*

* cited by examiner

*Primary Examiner*—Paul J. Killos
*Assistant Examiner*—Mahreen Chaudhry
(74) *Attorney, Agent, or Firm*—Oblon, Spivak, McClelland, Maier & Neustadt, P.C.

(57) ABSTRACT

There is provided a process for purification of N-(3,3-dimethylbutyl)-α-L-aspartyl-L-phenylalanine methyl ester comprising the step of contacting impure N-(3,3-dimethylbutyl)-α-L-aspartyl-L-phenylalanine methyl ester containing at least α-L-aspartyl-L-phenylalanine methyl ester as an impurity, with the mixed solvents having two layers of one layer given from at least one organic solvent which does not mix with water homogeneously and one layer of water to extract N-(3,3-dimethylbutyl)-α-L-aspartyl-L-phenylalanine methyl ester in the organic solvent layer.

In the present invention, the desired compound can be purified or recovered efficiently in a high yield without using burdensome steps or operations.

4 Claims, No Drawings

PROCESS FOR PURIFICATION OR RECOVERY OF SWEETENER

TECHNICAL FIELD OF INVENTION

The present invention relates to a novel process for purification or recovery of a sweetener having a high degree of sweetness, and more particularly, relates to a process for purification or recovery of N-(3,3-dimethylbutyl)-α-L-aspartyl-L-phenylalanine methyl ester represented by the following general formula (1) described in the Kohyou Patent Publication, Tokuhyouhei-JP-A-8-503206(503206/1996) from PCT.

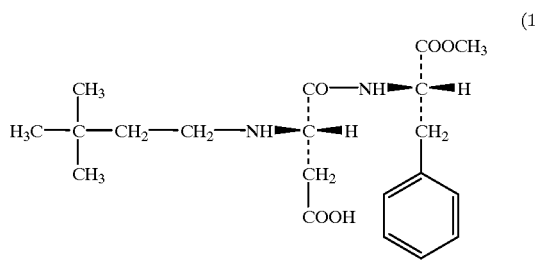

BACKGROUND OF ART

Since the compound in the present invention is synthesized by reacting α-L-aspartyl-L-phenylalanine methyl ester with 3,3-dimethylbutyl aldehyde as described in the publication, for example, Tokuhyouhei-JP-A-8-503206, EP Patent Publication WO95/30689, or etc., it is difficult to avoid the mixing of unreacted α-L-aspartyl-L-phenylalanine methyl ester into N-(3,3-dimethylbutyl)-α-L-aspartyl-L-phenylalanine methyl ester. Accordingly, it is most important to remove α-L-aspartyl-L-phenylalanine methyl ester for the purification of N-(3,3-dimethylbutyl)-α-L-aspartyl-L-phenylalanine methyl ester. It is described in the publication of Tokuhyouhei-JP-A-503206 that the compound in the present invention can be purified by a standard technique such as recrystallization and chromatography. The chromatography is not an appropriate technique for an industrial purification method. And, the recrystallization is in most common use for an industrial purification method, and however since the desired compound is dissolved in the mother liquor, and the dissolved compound is lost away, it is difficult to say that it is an efficient technique in view of the yield. Accordingly, a recovering method from the mother liquor is employed industrially by necessity to improve the yield. In the meantime, there is little difference between the solubility of α-L-aspartyl-L-phenylalanine methyl ester and the solubility of N-(3,3-dimethylbutyl)-α-L-aspartyl-L-phenylalanine methyl ester at a temperature of from 5 to 25° C. in the water which is usually employed for the solvent in the recrystallization of peptides and thus an amount of N-(3,3-dimethylbutyl)-α-L-aspartyl-L-phenylalanine methyl ester nearly equal to that of α-L-aspartyl-L-phenylalanine methyl ester is lost in the mother liquor through the recrystallization step. In addition, a recovering method from the mother liquor is not described in any specifications of the above-mentioned 2 prior patent publications. Typically, the object (desired) compound may be recovered by concentrating and cooling the mother liquor to crystallization, and however this recovering method requests burdensome steps or operations on the concentration, crystallization and separation, and further is not efficient also from the recovery rate (yield) thereof, because the object compound is lost in the mother liquor.

OBJECT OF INVENTION

The problem to be solved by the present invention, that is the object of the present invention, is to provide an effective process for purification or recovery of N-(3,3-dimethylbutyl)-α-L-aspartyl-L-phenylalanine methyl ester.

DISCLOSURE OF INVENTION

In order to solve the problem, the present inventors have studied earnestly a process to purify N-(3,3-dimethylbutyl)-α-L-aspartyl-L-phenylalanine methyl ester represented by the above-mentioned general formula containing at least α-L-aspartyl-L-phenylalanine methyl ester as an impurity, and also a process to recover the object compound from an aqueous solution of N-(3,3-dimethylbutyl)-α-L-aspartyl-L-phenylalanine methyl ester containing at least α-L-aspartyl-L-phenylalanine methyl ester as a dissolved substance, and consequently have found unexpectedly that high purity N-(3,3-dimethylbutyl)-α-L-aspartyl-L-phenylalanine methyl ester not containing α-L-aspartyl-L-phenylalanine methyl ester can be obtained by contacting N-(3,3-dimethylbutyl)-α-L-aspartyl-L-phenylalanine methyl ester containing at least α-L-aspartyl-L-phenylalanine methyl ester as an impurity, with the mixed solvents having two layers of one layer given from at least one organic solvent (one or more organic solvents) which does not mix (is immiscible) with water homogeneously and one layer of water to extract N-(3,3-dimethylbutyl)-α-L-aspartyl-L-phenylalanine methyl ester in the side of the organic solvent layer in the separated layers, and on the other hand, to extract α-L-aspartyl-L-phenylalanine methyl ester in the side of the water layer therein for selectivity. In addition, they have found that N-(3,3-dimethylbutyl)-α-L-aspartyl-L-phenylalanine methyl ester can be recovered from N-(3, 3-dimethylbutyl)-α-L-aspartyl-L-phenylalanine methyl ester containing α-L-aspartyl-L-phenylalanine methyl ester by contacting an aqueous solution of such impure N-(3,3-dimethylbutyl)-α-L-aspartyl-L-phenylalanine methyl ester containing α-L-aspartyl-L-phenylalanine methyl ester as a dissolved substance with at least one organic solvent which does not mix with water homogeneously to extract such desired compound in the side of the organic layer. The present invention has been completed based on the above findings.

Namely, the present invention is directed to a process for purification of N-(3,3-dimethylbutyl)-α-L-aspartyl-L-phenylalanine methyl ester represented by the above mentioned general formula comprising the step of: contacting impure N-(3,3-dimethylbutyl)-α-L-aspartyl-L-phenylalanine methyl ester containing at least α-L-aspartyl-L-phenylalanine methyl ester as an impurity, with the mixed solvents having two layers of one layer given from at least one organic solvent (one or more solvents) which does not mix (is immiscible) with water homogeneously and one layer of water to extract N-(3,3-dimethylbutyl)-α-L-aspartyl-L-phenylalanine methyl ester in the organic layer.

The present invention includes the following contents:

[1] The above purification process, wherein for the said at least one organic solvent (one or more solvents) which does not mix with water homogeneously, at least one organic solvent selected from the group consisting of toluene, ethyl acetate and butyl acetate is used.

[2] A process for recovery of N-(3,3-dimethylbutyl)-α-L-aspartyl-L-phenylalanine methyl ester represented by the above mentioned general formula (1) comprising the step of: contacting an aqueous solution of N-(3,3-dimethylbutyl)-α-L-aspartyl-L-phenylalanine methyl ester dissolving at least α-L-aspartyl-L-phenylalanine methyl ester as an impurity, with at least one organic solvent (one or more solvents) which does not mix with water homogeneously to dissolve and extract N-(3,3-dimethylbutyl)-α-L-aspartyl-L-phenylalanine methyl ester in the organic solvent layer.

[3] N-(3,3-dimethylbutyl)-α-L-aspartyl-L-phenylalanine methyl ester as obtained in the above any processes for the purification or recovery thereof.

EMBODIMENTS OF INVENTION

For the examples of organic solvents which do not mix (are immiscible) with water homogeneously usable for the present invention, aromatic hydrocarbons such as toluene and xylene, fatty acid esters such as ethyl acetate and butyl acetate, and halogenated hydrocarbons such as methylene chloride and chloroform are cited. Among them, toluene, ethyl acetate and butyl acetate are preferably employed in view of an industrial application.

As the organic solvent, any organic solvents which do not mix with water homogeneously may be employed in the present invention, and a mixture of plural organic solvents which may form a separated layer against the water layer in the solution can also be employed. For the mixed solvents having 2 layers, typically the mixed solvents forming 2 layers wherein one layer is separated from the water layer in the solution is employed. The mixed solvents forming 3 layers separated therein may be also employed on circumstances.

For the quantity used of the organic solvent (one or more solvents), there are no special limitations thereon. The yield is improved higher as the rate of the quantity used of the organic solvent goes up in comparison with the quantity used of water. In case that such extracting operations are repeated, the yield thereof may get close to 100% thereof without limit. It is no problems, of course that the solvent having no reactivities to the starting materials and the desired product, for example, acetic acid, methanol, dioxane, dimethylformamide, etc. may be mixed in the solution having 2 layers consisting of such organic solvent and water on condition that the 2 separated layers are maintained without decomposition.

Regarding the temperature for treatment in the process of the present invention, it is no problems that not higher than the temperature at the boiling point of the organic solvent used may be employed. And however, a decomposition of the desired product may be caused in the treatment stage at the too high temperature range, and therefore typically a temperature range of 0 to 100° C. is preferably selected.

On the time period for the treatment in the process of the present invention there are no special limitations thereon. And however, a decomposition of the product may be caused in the treatment under the too long time period, and therefore typically the treatment operated for 60 minutes or shorter is sufficient.

For the steps of purification method, the following aspects can be employed.

The crystals containing α-L-aspartyl-L-phenylalanine methyl ester are put into the separated 2 layers of the solution from a water layer and an organic layer obtained from one or more organic solvents immiscible with water homogeneously, and the mixture is stirred to dissolve the crystals. After confirmation of the fact that the crystals are perfectly dissolved in the solution, it is further stirred for a given time period. After that, the stirring is stopped, and after confirmation of the fact that the separated 2 layers are formed in the solution, one layer may be separated away from the other layer.

On the other hand, for the steps of the recovering method in the present invention, the following aspects can be employed.

To an aqueous solution (for example, crystallization mother liquor) dissolving both α-L-aspartyl-L-phenylalanine methyl ester and N-(3,3-dimethylbutyl)-α-L-aspartyl-L-phenylalanine methyl ester, at least one organic solvent (one or more solvents) is added and the mixture is stirred for a given time period. After that, the stirring is stopped, and after confirmation of the fact that the separated 2 layers are formed in the solution, one layer may be separated away from the other layer.

In the above both methods, in order to improve the yield higher, the organic solvent may be further added to the water layer and the extracting operations thereon may be repeated.

In the both methods, the organic layer taken out and obtained from the separated 2 layers in the solution may be concentrated under reduced pressure to the solid material to obtain N-(3,3-dimethylbutyl)-α-L-aspartyl-L-phenylalanine methyl ester which does not contain α-L-aspartyl-L-phenylalanine methyl ester. Moreover, in order to improve its purity by removing very small amount of impurities, thus obtained crystals may be subjected to recrystallization. In the crystallization mother liquor, α-L-aspartyl-L-phenylalanine methyl ester is not contained, and therefore it can be easily recycled, of course.

Preferred Embodiments

The present invention is illustrated specifically by referring to the following Examples.

EXAMPLE 1

The crystals consisting of 4.5 g of α-L-aspartyl-L-phenylalanine methyl ester and 10 g of N-(3,3-dimethylbutyl)-α-L-aspartyl-L-phenylalanine methyl ester were added to the mixed solvents consisting of 1000 ml of ethyl acetate and 500 ml of water, and the mixture was stirred at room temperature. The crystals were completely dissolved in the solution, and then the mixture was further stirred for 25 minutes. The mixture was allowed to stand for 5 minutes to make 2 layers separated in the solution. Thus obtained organic layer was washed with 100 ml of water and concentrated under reduced pressure to give 9.1 g of white crystals. In the crystals, α-L-aspartyl-L-phenylalanine methyl ester was not contained. The recovery yield of N-(3,3-dimethylbutyl)-α-L-aspartyl-L-phenylalanine methyl ester was 91%.

EXAMPLE 2

To the mixed solvents of 500 ml of toluene and 100 ml of water, the crystals consisting of 4.5 g of α-L-aspartyl-L-phenylalanine methyl ester and 10 g of N-(3,3-dimethylbutyl)-α-L-aspartyl-L-phenylalanine methyl ester were added, and thus obtained mixture was stirred at 50° C. After confirming the fact that the crystals have been dissolved completely in the solution, the mixture was further stirred for 10 minutes. The mixture was allowed to stand for 5 minutes to make 2 layers separated in the solution. Thus obtained organic layer was washed with 20 ml of water, and concentrated under reduced pressure to obtain 9.3 g of white crystals. In the crystals, α-L-aspartyl-L-phenylalanine methyl ester was not contained. The recovery yield of N-(3,3-dimethylbutyl)-α-L-aspartyl-L-phenylalanine methyl ester was 93%.

EXAMPLE 3

To the mixed solvents of 1000 ml of toluene and 100 ml of water, the crystals consisting of 4.5 g of α-L-aspartyl-L- phenylalanine methyl ester and 10 g of N-(3,3-dimethylbutyl)-α-L-aspartyl-L-phenylalanine methyl ester were added, and thus obtained mixture was stirred at 50° C. The crystals were dissolved completely in the solution, and then the mixture was further stirred for 10 minutes. The mixture was allowed to stand for 5 minutes to make 2 layers separated in the solution. Thus obtained organic layer was concentrated under reduced pressure to obtain 9.5 g of white crystals. Thus obtained crystals were recrystallized in the water to obtain 8.8 g of N-(3,3-dimethylbutyl)-α-L-aspartyl-L-phenylalanine methyl ester. In the crystals, α-L-aspartyl-L-phenylalanine methyl ester was not contained. The recovery yield thereof was 88%.

EXAMPLE 4

To 500 ml of aqueous solution in the concentrations of 0.9 g/dl of α-L-aspartyl-L-phenylalanine methyl ester and 0.9 g/dl of N-(3,3-dimethylbutyl)-α-L-aspartyl-L-phenylalanine methyl ester, 500 ml of ethyl acetate was added, and the mixture was stirred at room temperature for 10 minutes. The mixture was allowed to stand for 2 minutes to give 2 layers separated in the solution. To thus obtained water layer, 500 ml of ethyl acetate was added, and the operations were repeated in the same manner as above. Thus obtained organic layers were combined together, and concentrated under reduced pressure to obtain 4.3 g of N-(3,3-dimethylbutyl)-α-L-aspartyl-L-phenylalanine methyl ester in the crystalline form. In the crystals, α-L-aspartyl-L-phenylalanine methyl ester was not contained. The recovery yield thereof was 95%.

EXAMPLE 5

To the mixed solvents of 1000 ml of butyl acetate and 500 ml of water, the crystals consisting of 4.5 g of α-L-aspartyl-L-phenylalanine methyl ester and log of N-(3,3-dimethylbutyl)-α-L-aspartyl-L-phenylalanine methyl ester were added, and thus obtained mixture was stirred at room temperature. After confirming the fact that the crystals have been dissolved completely in the solution, the mixture was further stirred for 25 minutes. The mixture was allowed to stand for 5 minutes to make 2 layers separated in the solution. Thus obtained organic layer was washed with 100 ml of water, and concentrated under reduced pressure to obtain 9.0 g of white crystals. In the crystals, α-L-aspartyl-L-phenylalanine methyl ester was not contained. The recovery yield of N-(3,3-dimethylbutyl)-α-L-aspartyl-L-phenylalanine methyl ester was 90%.

EXAMPLE 6

An aqueous solution (500 ml) in the concentrations of 0.9 g/dl of α-L-aspartyl-L-phenylalanine methyl ester and 0.9 g/dl of N-(3,3-dimethylbutyl)-α-L-aspartyl-L-phenylalanine methyl ester was concentrated under reduced pressure to 100 ml of aqueous solution in the volume. To the solution 500 ml of toluene was added, and the mixture was stirred at 60° C. for 10 minutes. The mixture was allowed to stand for 2 minutes to give 2 layers separated in the solution. Thus obtained organic layer was washed with 100 ml of water. The organic layer was concentrated under reduced pressure to obtain 4.0 g of N-(3,3-dimethylbutyl)-α-L-aspartyl-L-phenylalanine methyl ester in the crystalline form. In the crystals, α-L-aspartyl-L-phenylalanine methyl ester was not contained. The recovery yield thereof was 89%.

Effects of Invention

Under the present invention, N-(3,3-dimethylbutyl)-α-L-aspartyl-L-phenylalanine methyl ester having a high degree of purity can be purified or recovered efficiently in a high yield without using burdensome steps or operations. The process in the present invention is preferably used for the purification or recovery thereof, particularly from the N-(3,3-dimethylbutyl)-α-L-aspartyl-L-phenylalanine methyl ester including at least α-L-aspartyl-L-phenylalanine methyl ester as an impurity.

What is claimed is:

1. A process for purification of N-(3, 3-dimethylbutyl)-α-L-aspartyl-L- phenylalanine methy ester comprising:

contacting impure N-(3,3-dimethybutyl)-α-L-aspartyl-L-phenylalanine methyl ester containing at least α-L-aspartyl-L-phenylalanine methyl ester as an impurity, with mixed solvents having two layers of one layer given from at least one organic solvent which does not mix with water homogenously and one layer of water to extract N-(3,3-dimethylbutyl)- α-L-aspartyl-L-phenylalamine methyl ester in the organic layer.

2. The process as defined in claim 1, wherein said at least one organic solvent which does not mix with water homogeneously is toluene.

3. The process as defined in claim 1, wherein said at least one organic solvent which does not mix with water homogeneously is at least one of ethyl acetate and butyl acetate.

4. A process for recovert of N-(3,3-dimethylbutyl)-α-L-aspartyl-L- phenylalanine methyl ester comprising:

contacting an aqueous solution of N-(3,3-dimethylbutyl)-α-L-aspartyl-L- phenylalanine methyl ester dissolving at least α-L-aspartyl-L-phenylalanine methyl ester as an impurity, with at least one organic solvent which does not mix with water homogenously to extract N-(3,3-dimethylbutyl)-α-L-phenylalanine methyl ester in the organic layer.

* * * * *

UNITED STATES PATENT AND TRADEMARK OFFICE
CERTIFICATE OF CORRECTION

PATENT NO. : 6,316,657 B1  
DATED : November 13, 2001  
INVENTOR(S) : Takemoto

Page 1 of 1

It is certified that error appears in the above-identified patent and that said Letters Patent is hereby corrected as shown below:

Title page,  
Item [63], the Related U.S. Application information should read:  
-- Related U.S. Application Data  
[63]   Continuation of application No. PCT/JP98/03682, filed on Aug. 19, 1998.

Item [30], the Foreign Application Priority information should read:  
-- Foreign Application Priority Data  
Sep. 12, 1997   (JP) .................................9-247941

Signed and Sealed this

Thirtieth Day of April, 2002

Attest:

Attesting Officer

JAMES E. ROGAN  
Director of the United States Patent and Trademark Office